(12) United States Patent  
Darwood

(10) Patent No.: US 12,090,082 B2
(45) Date of Patent: Sep. 17, 2024

(54) MEDICAL DRAINAGE TUBES

(71) Applicant: SALTS HEALTHCARE LIMITED, Birmingham (GB)

(72) Inventor: Richard Darwood, Birmingham (GB)

( * ) Notice: Subject to any disclaimer, the term of this patent is extended or adjusted under 35 U.S.C. 154(b) by 203 days.

(21) Appl. No.: 17/286,962

(22) PCT Filed: Oct. 18, 2019

(86) PCT No.: PCT/GB2019/052983
§ 371 (c)(1),
(2) Date: Apr. 20, 2021

(87) PCT Pub. No.: WO2020/084282
PCT Pub. Date: Apr. 30, 2020

(65) Prior Publication Data
US 2021/0386578 A1 Dec. 16, 2021

(30) Foreign Application Priority Data
Oct. 25, 2018 (GB) .................................... 1817375

(51) Int. Cl.
*A61F 5/44* (2006.01)
*A61F 5/445* (2006.01)
*A61M 25/00* (2006.01)

(52) U.S. Cl.
CPC ............ *A61F 5/4404* (2013.01); *A61F 5/445* (2013.01); *A61M 25/0017* (2013.01);
(Continued)

(58) Field of Classification Search
CPC ... A61F 5/4404; A61F 5/445; A61M 25/0017; A61M 2202/0496; A61M 2205/0227; A61M 2205/583
See application file for complete search history.

(56) References Cited

U.S. PATENT DOCUMENTS 3,818,895 A 6/1974 Stewart
4,384,485 A 5/1983 Layton et al.
(Continued)

FOREIGN PATENT DOCUMENTS

CN 201271310 Y 7/2009
EP 1774985 A1 4/2007
(Continued)

OTHER PUBLICATIONS

International Search Report and Written Opinion associated with international application No. PCT/GB2019/052983, mailed Jan. 20, 2020 (listed here, but submitted with 371 application filing).
(Continued)

*Primary Examiner* — Leslie A Lopez
*Assistant Examiner* — Timothy L Flynn
(74) *Attorney, Agent, or Firm* — Leydig, Voit & Mayer, Ltd.

(57) ABSTRACT

A medical drainage tube for transporting liquid from a liquid source to a liquid storage device, the medical drainage tube includes an inner surface which defines a lumen; an inlet for coupling to a liquid source and for receiving liquid into the lumen from the liquid source; an outlet for coupling to a liquid storage device and for transporting the received liquid from the lumen to the liquid storage device; and an indicator including an indicating agent which, when the medical drainage tube is in use, is configured to dissolve after being exposed to the liquid for at least 24 hours, thereby providing a trigger which notifies a user that the medical drainage tube requires replacement.

22 Claims, 3 Drawing Sheets

(52) U.S. Cl.
 CPC .............. *A61M 2202/0496* (2013.01); *A61M 2205/0227* (2013.01); *A61M 2205/583* (2013.01)

(56) References Cited

U.S. PATENT DOCUMENTS

| | | | |
|---|---|---|---|
| 4,872,868 A * | 10/1989 | Chevallier | A61F 5/4404 600/580 |
| 7,785,299 B2 | 8/2010 | Crawford et al. | |
| 9,265,865 B2 | 2/2016 | Hixon et al. | |
| 9,746,421 B2 * | 8/2017 | Heacock | G01N 31/229 |
| 2008/0004578 A1 | 1/2008 | Hixon et al. | |
| 2010/0211032 A1 * | 8/2010 | Tsai | A61F 5/453 604/319 |
| 2014/0356901 A1 * | 12/2014 | Peppou | A61B 5/6852 427/2.25 |
| 2018/0338747 A1 | 11/2018 | Joshi et al. | |
| 2021/0085853 A1 * | 3/2021 | Chen | A61M 3/0208 |
| 2021/0290207 A1 * | 9/2021 | Locke | A61M 1/95 |

FOREIGN PATENT DOCUMENTS

| | | |
|---|---|---|
| WO | WO 2014/077886 A1 | 5/2014 |
| WO | WO 2016/126555 A1 | 8/2016 |
| WO | WO 2019/060309 A | 3/2019 |

OTHER PUBLICATIONS

Search Report of UK Intellectual Property Office associated with application No. GB1817375.7, issued Apr. 16, 2019.
Search Report of UK Intellectual Property Office associated with application No. GB1915126.5, issued Apr. 1, 2020.
Notice of Reasons for Rejection associated with Japanese Patent Application No. 2021-521977, mailed Jun. 20, 2023.
Office Action associated with Canadian Patent Application No. 3,116,949, mailed Oct. 20, 2023.

* cited by examiner

MEDICAL DRAINAGE TUBES

CROSS REFERENCE TO RELATED APPLICATIONS

This application is a U.S. National Stage Application under 35 U.S.C. § 371 of International Application No. PCT/GB2019/052983, filed Oct. 18, 2019, which claims the benefit of and priority to GB Patent Application No. 1817375.7 filed Oct. 25, 2018, each of which is hereby incorporated by reference in its entirety to the extent not inconsistent herein.

Embodiments of the present invention relate to medical drainage tubes and particularly, although not exclusively, to medical drainage tubes for use in medical devices. For instance, embodiments of the invention may relate to medical drainage tubes for use in night drainage systems, such as urostomy night drainage systems. Embodiments of the invention may also relate to medical drainage tubes for use in conventional catheter systems.

It is an object of the present invention to seek to provide medical devices (especially those used to transport bodily fluids such as urine) having improved cleanliness.

According to a first aspect of the invention, we provide a medical drainage tube for transporting liquid (such as urine) from a liquid source to a liquid storage device, the medical drainage tube including:
   an inner surface defining a lumen;
   an inlet for coupling to a liquid source and for receiving liquid into the lumen from the liquid source;
   an outlet for coupling to a liquid storage device and for transporting the received liquid from the lumen to the liquid storage device; and
   an indicator including an indicating agent which, when the medical drainage tube is in use, is configured to dissolve after being exposed to the liquid for at least 24 hours, thereby providing a trigger which notifies a user that the medical drainage tube requires replacement.

The liquid may be a bodily fluid. The liquid may be urine.

In use, the temperature of the liquid at the point of contacting the indicating agent is at or slightly below normal body temperature (i.e. 37.5° C.). This is because the liquid contacts the indicating agent shortly after leaving the body. The temperature of the liquid at the point of contacting the indicating agent may therefore be approximately 35° C. to approximately 37.5° C.

The indicating agent may be configured to dissolve after being exposed to the liquid for at least 48 hours or at least 72 hours or at least 96 hours or at least 120 hours or at least 144 hours or at least 168 hours.

The indicating agent may be configured to dissolve after being exposed to the liquid for up to 336 hours. After 336 hours has elapsed, the medical drainage tube will almost certainly require replacement to maintain recommended hygiene standards.

Thus, once the indicating agent has dissolved, the trigger alerts the user that the medical drainage tube requires replacement. Once the medical drainage tube has been replaced the overall cleanliness of the medical device will have been improved.

The indicator may include a further indicating agent configured to dissolve after being exposed to the liquid. The further indicating agent may have a different rate of dissolution in the liquid when compared to the rate of dissolution of the indicating agent in the same liquid. For example, the further indicating agent may dissolve slower than the indicating agent.

The medical drainage tube may further comprise a cavity inside which the or each indicating agent is located. The cavity may be separate from the lumen.

The cavity may be in liquid communication with the lumen via a first liquid flow path.

Additionally, the cavity may be in liquid communication with the lumen via a second liquid flow path.

The or each indicating agent may be secured or may be securable to an inner surface of the cavity.

The or each indicating agent may be located within the lumen.

The or each indicating agent may be secured or may be securable to the inner surface of the medical drainage tube.

The or each indicating agent may be in the form of any one of a pellet, a tablet, a capsule, a sphere or a lozenge.

The or each indicating agent may be in the form of a strip of material having a length L.

The or each indicating agent may have a first portion and a second portion spaced along the length L from the first portion, wherein a width and/or a thickness of the first portion is narrower than a width and/or a thickness of the second portion.

The medical drainage tube may further comprise a measurement device associated with the or each indicating agent.

The measurement device may include a series of graduations, e.g. in the form of a ruler.

The measurement device may be provided on a surface of the medical drainage tube. For instance, the measurement device may be provided on the inner surface or an outer surface of the medical drainage tube or on the inner surface or an outer surface of the cavity. Alternatively, the measurement device may be formed into the indicating agent and/or any further indicating agent.

The or each indicating agent may include a water soluble polymer, such as polyvinyl alcohol (PVOH).

According to a second aspect of the invention, we provide a medical drainage tube for transporting liquid (such as urine) from a liquid source to a liquid storage device, the medical drainage tube including:
   an inner surface defining a lumen;
   an inlet for coupling to a liquid source and for receiving liquid into the lumen from the liquid source;
   an outlet for coupling to a liquid storage device and for transporting the received liquid from the lumen to the liquid storage device; and
   an indicator configured to provide a trigger once a predetermined volume of liquid has passed between the inlet and the outlet, wherein, in use, the trigger notifies a user that the medical drainage tube requires replacement.

The second aspect of the invention may include any of the optional features of the first aspect of the invention.

According to a third aspect of the invention, we provide a kit including:
   a liquid storage device; and
   a medical drainage tube according to either of the preceding aspects of the invention for transporting liquid from a liquid source to the liquid storage device.

The kit may include a liquid source.

The liquid storage device and the medical drainage tube may be discrete components. Alternatively, the liquid storage device and the medical drainage tube may be integrally formed.

The liquid source may include a urostomy bag.

The kit may comprise components of a night drainage system.

Embodiments of the invention will now be described with reference to the accompanying drawings, of which:

Figure 1:
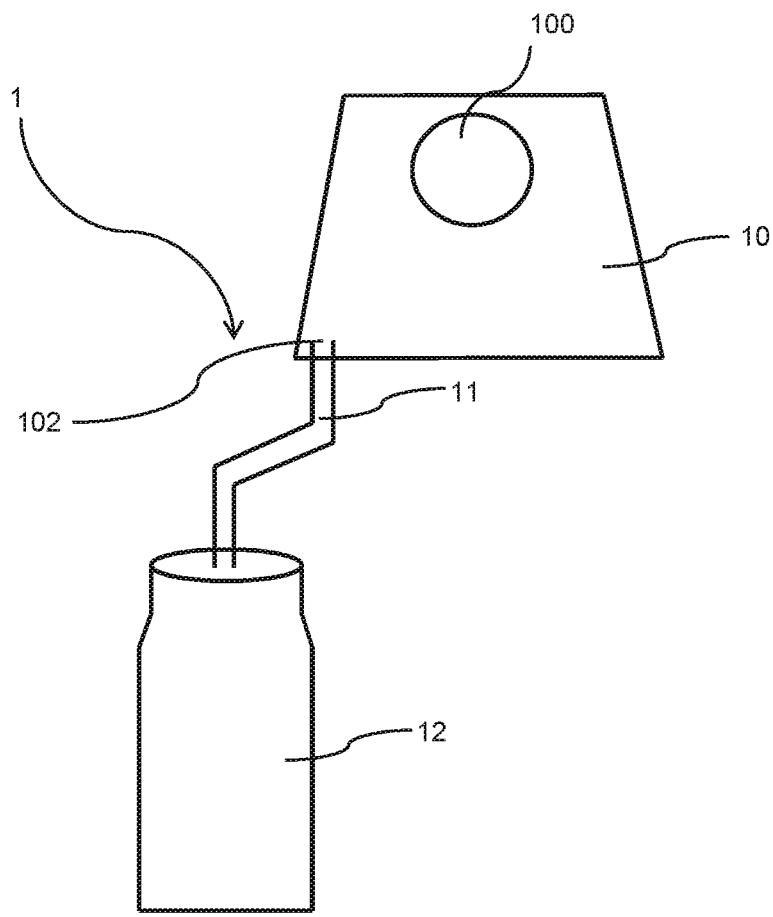
FIG. 1 is a schematic representation of a prior art night drainage system.

Referring first to FIG. 1 there is shown a prior art night drainage system, indicated generally at 1. The night drainage system 1 comprises a liquid source 10, a medical drainage tube 11 and a liquid storage device 12. The liquid source 10 may be in the form of a urostomy bag. Night drainage systems 1 are advantageous in that they can allow the user to connect their urostomy bag to a liquid storage device 12 during the night. The liquid storage device 12 can hold a larger volume of urine than the urostomy bag. This can therefore help the user to get uninterrupted sleep because they do not need to wake up periodically during the night to empty their urostomy bag of urine.

Instead, urine collects (via the urostomy bag and the drainage tube 11) in the liquid storage device 12 overnight and can be disposed of when the user wakes up.

The urostomy bag defines an opening 100 through which urine can be received therein from a user's stoma. Urostomy bags typically have an outlet 102 at the bottom to allow the user to drain the bag during the day. During the night the medical drainage tube 11 may be connected to the outlet 102 so that urine can be transported from the urostomy bag and into the liquid storage device 12 via the medical drainage tube 11. The liquid storage device 12 may be in the form of a container, such as a bottle.

Referring now to FIGS. 2 to 8 there are shown various embodiments of the present invention.

Figure 2:
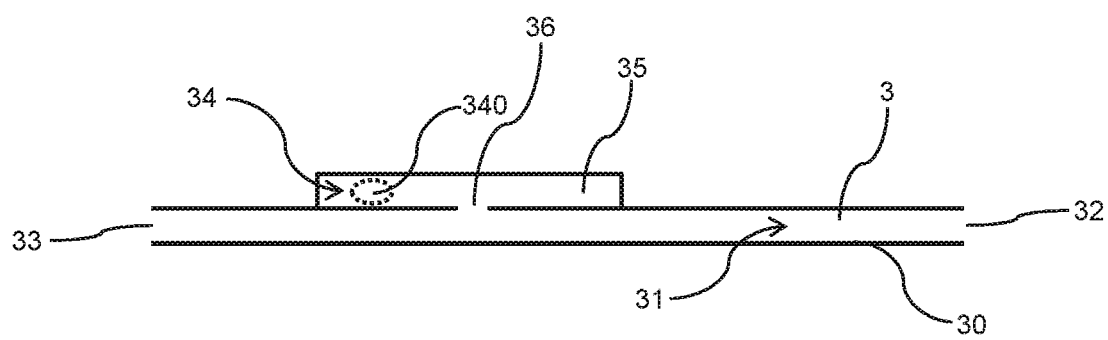
FIG. 2 is a schematic representation of a drainage tube according to a first embodiment of the invention.

FIG. 2 shows a medical drainage tube 3 for transporting liquid from the liquid source 10 to the liquid storage device 12. The medical drainage tube 3 includes an inner surface 30 which defines a lumen 31. The medical drainage tube 3 also includes an inlet 32 for coupling to the liquid source 10 and an outlet 33 for coupling to the liquid storage device 12. The medical drainage tube 3 further includes an indicator, designated generally at 34. The indicator 34 is configured to provide a trigger which notifies the user that the medical drainage tube 3 is due for replacement. The user can therefore replace the medical drainage tube 3 to ensure that the medical device, i.e. the night drainage system, remains hygienic.

The indicator 34 includes an indicating agent 340 configured to dissolve after being exposed to the liquid for at least 24 hours, thereby providing the trigger. The trigger is provided once the indicating agent 340 is no longer visible to the user.

In some embodiments, the indicating agent 340 may include a water soluble polymer. Non-limiting examples of suitable water soluble polymers include polyvinyl alcohol (PVOH), polyacrylic acid (PAA) and copolymers thereof, polyacrylamides (PAM) and polyethylene glycols (PEG). It is known in the art how to modify the dissolution rates of such water soluble polymers. Water soluble polymers having varying dissolution rates are commercially available. Accordingly, it is straightforward to source and configure polymers that dissolve once they have been in contact with liquid having a temperature of approximately 35° C. to approximately 37.5° C. for a predetermined time. For the avoidance of doubt, the predetermined time is at least 24 hours.

The medical drainage tube 3 may comprise a cavity 35 inside which the indicating agent 340 is located, the cavity 35 being separate from the lumen 31. In some embodiments, the cavity 35 may be in liquid communication with the lumen 31 via a first liquid flow path 36. Thus, in use, liquid passing between the inlet 32 and the outlet 33 can flow into the cavity 35 via the first liquid flow path 36. Once the indicating agent 340 has been exposed to the liquid for at least 24 hours it will dissolve such that it is no longer visible to the user, thereby providing the trigger that the medical drainage tube 3 needs to be replaced.

In some embodiments, the indicating agent 340 may be secured to an inner surface of the cavity 35. For instance, the indicating agent 340 may be bonded to an inner surface of the cavity 35 by adhesive. In embodiments where the indicating agent 340 is not secured to an inner surface of the cavity 35 (e.g. embodiments where the indicating agent 340 is freely moveable within the cavity 35) the first liquid flow path 36 may be at least partially occluded, e.g. by a water permeable filter (not shown), to prevent the indicating agent 340 from travelling between the cavity 35 and the lumen 31.

The indicating agent 340 of FIG. 2 is in the form of a pellet. However, in some embodiments, the indicating agent 340 may be in the form of any one of a tablet, a capsule, a sphere or a lozenge.

Figure 3:
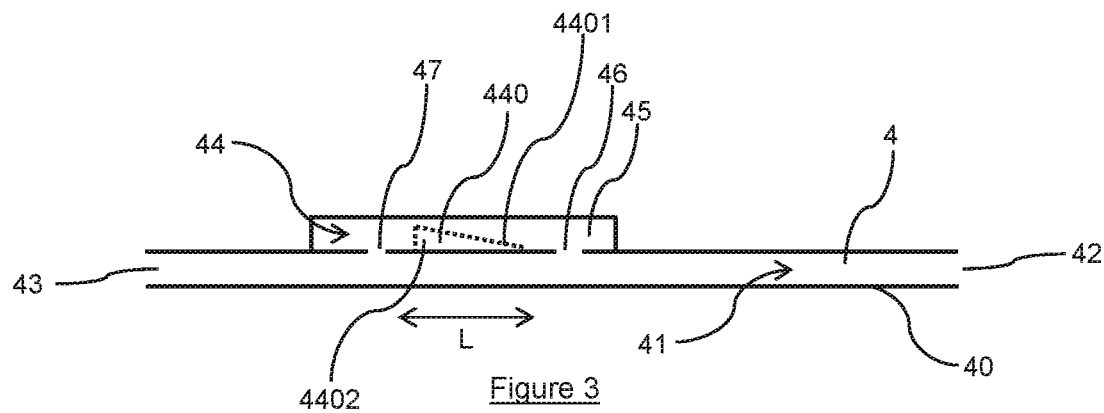
FIG. 3 is a schematic representation of a drainage tube according to a second embodiment of the invention.

FIG. 3 shows a medical drainage tube 4 for transporting liquid from the liquid source 10 to the liquid storage device 12. The medical drainage tube 4 includes an inner surface 40 which defines a lumen 41. The medical drainage tube 4 also includes an inlet 42 for coupling to the liquid source 10 and an outlet 43 for coupling to the liquid storage device 12. The medical drainage tube 4 further includes an indicator, designated generally at 44, that is configured to provide a trigger which notifies the user that the medical drainage tube 4 is due for replacement. The user can therefore replace the medical drainage tube 4 to ensure that the medical device remains hygienic.

The indicator 44 may include an indicating agent 440 configured to dissolve after being exposed to liquid for a minimum of 24 hours in the same manner as the indicating agent 340 of FIG. 2. The difference between the indicating agents 340, 440 is that the indicating agent 440 is provided in the form of a strip of material having a length L.

The medical drainage tube 4 may comprise a cavity 45 inside which the indicating agent 440 is located, the cavity 45 being separate from the lumen 41. The cavity 45 may be in liquid communication with the lumen 41 via a first liquid flow path 46 and a second liquid flow path 47. Thus, in use, liquid passing between the inlet 42 and the outlet 43 can flow into the cavity 45 via the first liquid flow path 46 and from the cavity 45 via the second liquid flow path 47.

The indicating agent 440 may be secured to an inner surface of the cavity 45. For instance, the indicating agent 440 may be bonded to an inner surface of the cavity 45 by adhesive. In embodiments where the indicating agent 440 is not secured to an inner surface of the cavity 45 (e.g. embodiments where the indicating agent 440 is freely moveable within the cavity 45) the first liquid flow path 46 and/or the second liquid flow path 47 may be at least partially occluded, e.g. by a water permeable filter (not shown), to prevent the indicating agent 440 from travelling between the cavity 45 and the lumen 41.

The indicating agent 440 may be located between the first liquid flow path 46 and the second liquid flow path 47. Thus, liquid is encouraged to flow across the indicating agent 440 as it passes through the cavity 45.

The indicating agent 440 may be disposed relative to the lumen 41 such that its length L is substantially aligned with the longitudinal axis of the lumen 41.

The indicating agent 440 may have a first portion 4401 and a second portion 4402 spaced along the length L from the first portion 4401, wherein a thickness of the first portion 4401 is narrower than a thickness of the second portion 4402. Alternatively or additionally, a width of the first portion 4401 may be narrower than a width of the second portion 4402. For instance, the thickness and/or width of the indicating agent 440 at the first portion 4401 may be approximately 0.1 mm. The thickness and/or width of the indicating agent 440 at the second portion 4402 may be approximately 2 mm. In such embodiments, the indicating agent 440 at the first portion 4401 may dissolve faster than the indicating agent 440 at the second portion 4402. This means that the indicating agent 440 dissolves from one end (i.e. the first portion 4401) towards the other end (i.e. the second portion 4402). Advantageously, the indicating agent 440 may be associated with a measurement device (described in more detail below) to provide the user with advanced warning with regard to the period of time that remains before the medical drainage tube 4 requires replacing.

Figure 4:
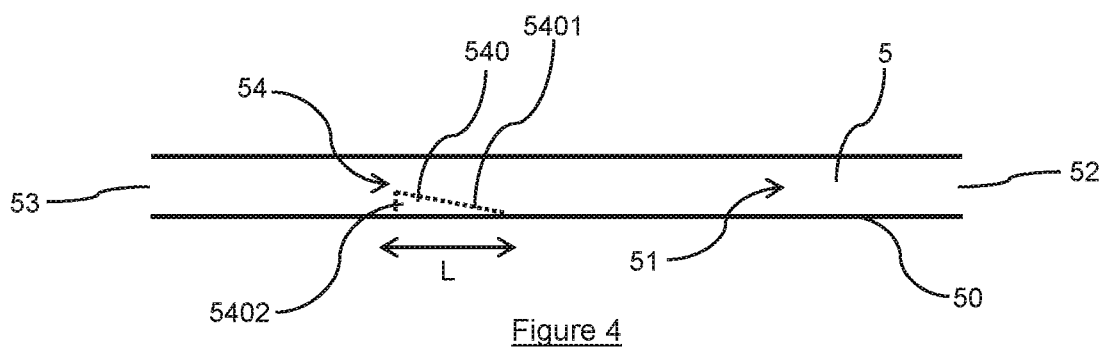
FIG. 4 is a schematic representation of a drainage tube according to a third embodiment of the invention.

FIG. 4 shows a medical drainage tube 5 for transporting liquid from the liquid source 10 to the liquid storage device 12. The medical drainage tube 5 includes an inner surface 50 which defines a lumen 51. The medical drainage tube 5 also includes an inlet 52 for coupling to the liquid source 10 and an outlet 53 for coupling to the liquid storage device 12. The medical drainage tube 5 further includes an indicator, designated generally at 54, that is configured to provide a trigger which notifies the user that the medical drainage tube 5 is due for replacement. The user can therefore replace the medical drainage tube 5 to ensure that the medical device remains hygienic.

The indicator 54 may include an indicating agent 540 configured to dissolve after being exposed to liquid for a minimum of 24 hours in the same manner as the previously described indicating agents 340, 440. The indicating agent 540 may be provided in the form of a strip of material having a length L.

The indicating agent 540 may be located within the lumen 51. In such embodiments, the indicating agent 540 may be secured to the inner surface 50 of the medical drainage tube 5. For instance, the indicating agent 540 may be bonded to the inner surface 50 of the medical drainage tube 5 by adhesive.

The indicating agent 540 may be disposed relative to the lumen 51 such that its length L is substantially aligned with the longitudinal axis of the lumen 51.

The indicating agent 540 may have a first portion 5401 and a second portion 5402 spaced along the length L from the first portion 5401, wherein a thickness of the first portion 5401 is narrower than a thickness of the second portion 5402. Alternatively or additionally, a width of the first portion 5401 may be narrower than a width of the second portion 5402. For instance, the thickness and/or width of the indicating agent 540 at the first portion 5401 may be approximately 0.1 mm. The thickness and/or width of the indicating agent 540 at the second portion 5402 may be approximately 2 mm. In such embodiments, the indicating agent 540 at the first portion 5401 may dissolve faster than the indicating agent 540 at the second portion 5402. The advantages of such a configuration have been previously explained.

Figure 5:
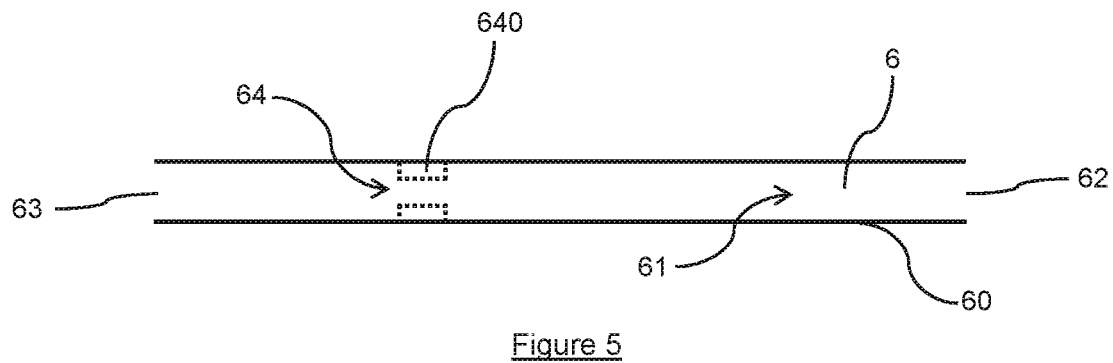
FIG. 5 is a schematic representation of a drainage tube according to a fourth embodiment of the invention.

FIG. 5 shows a medical drainage tube 6 for transporting liquid from the liquid source 10 to the liquid storage device 12. The medical drainage tube 6 includes an inner surface 60 which defines a lumen 61. The medical drainage tube 6 also includes an inlet 62 for coupling to the liquid source 10 and an outlet 63 for coupling to the liquid storage device 12. The medical drainage tube 6 further includes an indicator, designated generally at 64, that is configured to provide a trigger which notifies the user that the medical drainage tube 6 is due for replacement.

The indicating agent is 640 is located within the lumen 61 in a similar way to the indicating agent 540 of FIG. 4. As illustrated, however, the indicating agent 640 may be disposed relative to the lumen 61 such that its length L extends around at least a part of the inner wall of the lumen 61. The length L of the indicating agent 640 may therefore be substantially orthogonal to the longitudinal axis of the lumen 61. In some embodiments, the indicating agent 640 may extend around the entire inner wall of the lumen 61 such that the indicating agent 640 is in the form of a ring. The indicating agent 640 may have narrow and wide portions as in previous embodiments.

Figure 6:
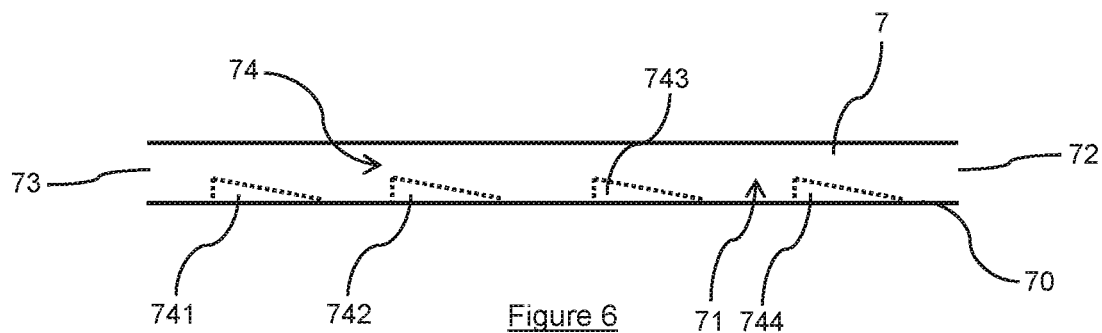
FIG. 6 is a schematic representation of a drainage tube according to a fifth embodiment of the invention.

FIG. 6 shows a medical drainage tube 7 including an inner surface 70 which defines a lumen 71. The medical drainage tube 7 also includes an inlet 72, an outlet 73 and an indicator, designated generally at 74. The configuration of FIG. 6 is similar to that shown in FIG. 4, with the exception that the indicator includes a first indicating agent 741, a second indicating agent 742, a third indicating agent 743 and a fourth indicating agent 744.

Figure 7:
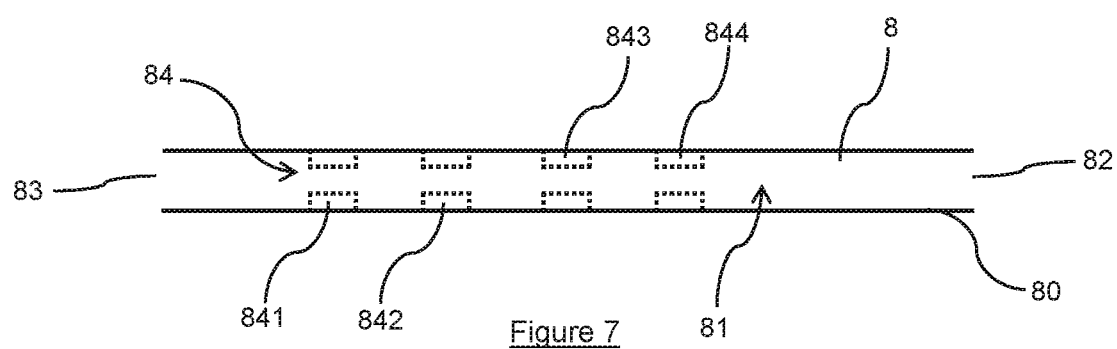
FIG. 7 is a schematic representation of a drainage tube according to a sixth embodiment of the invention.

FIG. 7 shows a medical drainage tube 8 including an inner surface 80 which defines a lumen 81. The medical drainage tube 8 also includes an inlet 82, an outlet 83 and an indicator, designated generally at 84. The configuration of FIG. 7 is similar to that shown in FIG. 5, with the exception that the indicator includes a first indicating agent 841, a second indicating agent 842, a third indicating agent 843 and a fourth indicating agent 844.

The indicating agents 741, 742, 743, 744; 841, 842, 843, 844 may be configured to have different dissolution rates to one another. For example, the first indicating agent 741; 841 may dissolve after having been exposed to liquid for 24 hours, the second indicating agent 742; 842 may dissolve after having been exposed to liquid for 48 hours, the third indicating agent 743; 843 may dissolve after having been exposed to liquid for 72 hours and the fourth indicating agent 744; 844 may dissolve after having been exposed to liquid for 96 hours.

Accordingly, the embodiments of FIGS. 6 and 7 provide information which can notify the user how long the medical drainage tubes 7; 8 have been in use.

Advantageously, this information can provide the user with an advance warning as to when the medical drainage tube will require replacement.

Although four indicating agents are shown in FIGS. 6 and 7, it is to be appreciated that in some embodiments fewer or greater than four (e.g. two, six etc.) indicating agents may be present.

In some embodiments, multiple indicating agents may be provided in a cavity rather than within the lumen of a medical drainage tube. For instance, multiple indicating agents may be provided in the cavities 35; 45 shown in FIGS. 2 and 3, respectively. The indicating agents may have differing dissolutions rates. For instance, a first indicating agent may dissolve after being exposed to liquid for 24 hours, a second indicating agent may dissolve after being exposed to liquid for 48 hours, a third indicating agent may dissolve after being exposed to liquid for 72 hours and so on. This arrangement thereby provides a countdown to inform the user how long has elapsed since the medical drainage tube was first used and/or how long remains before the medical drainage tube needs to be replaced.

Figure 8:
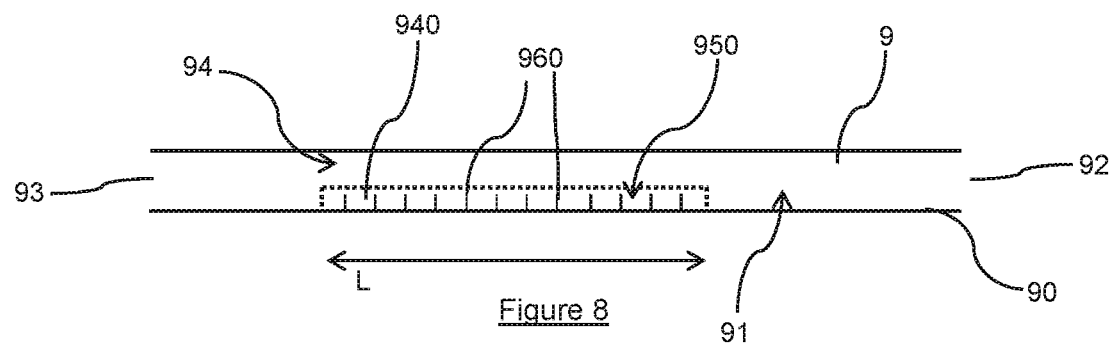
FIG. 8 is a schematic representation of a drainage tube according to a seventh embodiment of the invention.

FIG. 8 shows a medical drainage tube 9 including an inner surface 90 which defines a lumen 91. The medical drainage tube 9 also includes an inlet 92, an outlet 93 and an indicator, designated generally at 94. The indicator 94 includes an indicating agent 940 which may be in the form of a strip having a length L. The indicating agent 940 may be configured such that it dissolves from one end to the other. This may be achieved by varying the amount of the dissolvable species (e.g. the water soluble polymer) along the length L of the indicating agent 940.

A measurement device, indicated generally at 950, may be associated with the indicating agent 940. The measurement device 950 may include a series of graduations 960. The gap between the graduations 960 may represent a predetermined time period, e.g. 24 hours. Accordingly, the user can determine from the measurement device 950 how long is left before the drainage tube 94 will require replacing.

The measurement device 950 may be separate from the indicating agent 940. For instance, the measurement device 950 may be provided on the medical drainage tube 94. Alternatively, the measurement device 950 may be formed on the indicating agent 940. For instance, the indicating agent 940 may comprise ridges and/or indentations (representing the graduations 960) along the length L thereof.

Features from one embodiment may be combined with features from another embodiment without departing from the scope of the invention. For instance, the measurement device 950 may be included on any one of the medical drainages tubes described herein.

Indicating Agent(s)

The or each indicating agent may include a water soluble polymer, such as polyvinyl alcohol (PVOH), polyacrylic acid (PAA) and copolymers thereof, polyacrylamides (PAM) and polyethylene glycols (PEG).

It is well known that there are many factors that affect the dissolution rate of a water soluble polymer. These factors include but are not limited to:
 the composition of the water soluble polymer;
 the composition of the solvent;
 the temperature of the solvent;
 the size and/or shape of the water soluble polymer;
 whether or not there is washing (i.e. agitation) of the water soluble polymer, e.g. by the solvent;
 the molecular weight (i.e. degree of polymerisation) of the water soluble polymer; and
 the degree of hydrolysis of the water soluble polymer.

The temperature of the liquid will be approximately 35° C. to approximately 37.5° C. when it comes into contact with the or each indicating agent. Therefore, when the kit is in use, the temperature of the liquid is nominally constant. With this in mind, it is straightforward for the skilled person to select and configure a water soluble polymer such that it will dissolve in the liquid after the water soluble polymer has been exposed to the liquid for at least 24 hours.

Suitable non-limiting examples of water soluble polymers may include partially hydrolysed polyvinyl alcohols having the trade name KURARAY POVAL which can be obtained from Kuraray Co., Limited.

As will be understood by the skilled person, the term "thickness" is intended to refer to the height of the indicating agent from the surface upon which it is attached and the term "width" is intended to refer to the distance between the edges of the indicating agent across the surface upon which it is attached in a direction generally perpendicular to the length L.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

Although certain example embodiments of the invention have been described, the scope of the appended claims is not intended to be limited solely to these embodiments. The claims are to be construed literally, purposively, and/or to encompass equivalents.

The invention claimed is:

1. A medical drainage tube for transporting liquid from a liquid source to a liquid storage device, the medical drainage tube including:
 an inner surface defining a lumen;
 an inlet for coupling to the liquid source and for receiving liquid into the lumen from the liquid source;
 an outlet for coupling to the liquid storage device and for transporting the received liquid from the lumen to the liquid storage device; and
 a water soluble indicator which, when the medical drainage tube is in use, is configured to dissolve after being exposed to the liquid for at least 24 hours, thereby providing a trigger which notifies a user that the medical drainage tube requires replacement;
 wherein the indicator is in the form of:
  (i) a protrusion extending from a surface of the device into a flow path of the liquid; or
  (ii) a discrete object trapped within the lumen, or within a cavity in fluid communication with the lumen; and
 wherein the indicator is configured such that a visible reduction in a size of the protrusion or the discrete object as a result of contact with the received liquid is the trigger which notifies the user that the medical drainage tube requires replacement.

2. A medical drainage tube according to claim 1, wherein the indicator comprises a first water soluble polymer and a further indicating agent which is configured to dissolve after being exposed to the liquid.

3. A medical drainage tube according to claim 2, wherein the further indicating agent has a different rate of dissolution in the liquid than that of the first water soluble polymer.

4. A medical drainage tube according to claim 1, wherein the indicator is a discrete object trapped within the cavity in fluid communication with the lumen.

5. A medical drainage tube according to claim 4, wherein the cavity is in liquid communication with the lumen via a first liquid flow path.

6. A medical drainage tube according to claim 5, wherein the cavity is in liquid communication with the lumen via a second liquid flow path.

7. A medical drainage tube according to claim 4, wherein the indicator is secured or is securable to an inner surface of the cavity.

8. A medical drainage tube according to claim 1, wherein the indicator is located within the lumen.

9. A medical drainage tube according to claim 8, wherein the indicator is secured or is securable to the inner surface thereof.

10. A medical drainage tube according to claim 1, wherein the indicator is in the form of any one of a pellet, a tablet, a capsule, a sphere or a lozenge.

11. A medical drainage tube according to claim 1, wherein the indicator is in the form of a strip of material having a length L.

12. A medical drainage tube according to claim 11, wherein the indicator has a first portion and a second portion spaced along the length L from the first portion, wherein a width and/or thickness of the first portion is narrower than a width and/or thickness of the second portion.

13. A medical drainage tube according to claim 11, further comprising a measurement device associated with the indicator.

14. A medical drainage tube according to claim 13, wherein the measurement device includes a series of graduations.

15. A medical drainage tube according to claim 1, wherein the indicator comprises a water soluble polymer.

16. A medical drainage tube according to claim 1, wherein the indicator comprises a biopolymer.

17. A medical drainage tube according to claim 16, wherein the biopolymer comprises polyvinyl alcohol (PVOH), polyacrylic acid (PAA), polyacrylamides (PAM), polyethylene glycols (PEG), and/or combinations thereof.

18. A kit including:
   a liquid storage device; and
   a medical drainage tube according to claim 1 for transporting liquid from a liquid source to the liquid storage device.

19. A kit according to claim 18, wherein the liquid storage device and the medical drainage tube are discrete components.

20. A kit according to claim 18, wherein the liquid storage device and the medical drainage tube are integrally formed.

21. A kit according to claim 18, further including a liquid source.

22. A kit according to claim 21, wherein the liquid source includes a urostomy bag.

* * * * *